(12) United States Patent
Willmann et al.

(10) Patent No.: US 7,539,607 B2
(45) Date of Patent: May 26, 2009

(54) COMPUTER SYSTEM AND METHOD OF CALCULATING A PHARMACOKINETIC BEHAVIOR OF A CHEMICAL SUBSTANCE IN INSECTS

(75) Inventors: Stefan Willmann, Düsseldorf (DE); Walter Schmitt, Neuss (DE)

(73) Assignee: Bayer Technology Services GmbH, Leverkusen (DE)

( * ) Notice: Subject to any disclaimer, the term of this patent is extended or adjusted under 35 U.S.C. 154(b) by 804 days.

(21) Appl. No.: 10/714,791

(22) Filed: Nov. 14, 2003

(65) Prior Publication Data

US 2004/0172230 A1 Sep. 2, 2004

(30) Foreign Application Priority Data

Dec. 3, 2002 (DE) ................. 102 56 315

(51) Int. Cl.
*G06F 1/00* (2006.01)
(52) U.S. Cl. ............... 703/11; 702/19; 702/20; 703/13; 707/102
(58) Field of Classification Search ............ None
See application file for complete search history.

(56) References Cited

U.S. PATENT DOCUMENTS

| 5,751,605 A | 5/1998 | Hurst et al. ............ 364/496 |
| 2002/0002447 A1* | 1/2002 | Keane ..................... 703/11 |
| 2005/0119832 A1* | 6/2005 | Schmitt et al. ............ 702/19 |

FOREIGN PATENT DOCUMENTS

| EP | 1426763 A1 * | 6/2004 |
| JP | 2004238390 | * 8/2004 |
| WO | WO 00/15178 | 3/2000 |
| WO | WO 02/10742 | 2/2002 |
| WO | WO03048720 | * 6/2003 |

OTHER PUBLICATIONS

Norris D et al, "Development of predictive pharamacokinetic simulation models for drug discovery", Journal of Controlled Release, Elsevier Science Publishers, B.V. Amsterdam, NL, Bd. 65, Nor. 1-2, Mar. 2000 ,pp. 55-62.
Bernillon P, et al, "Statistical issues in toxicokinetic modeling: A Bayesian perspective", Environmental Health Perspectives 2000, United States, Bd. 108, Nr. SUPPL. 5, 2000, pp. 883-887, p. 891.
Rowland M, "Physiologic pharmacokinetic models and interanimal species scaling", Pharmacology and Therapeutics 1985 United Kingdom, Bd. 29, Nr. 1, 1985, pp. 49-68.

* cited by examiner

*Primary Examiner*—Mary K Zeman
(74) *Attorney, Agent, or Firm*—Norris McLaughlin & Marcus, PA; Christa Hildebrand

(57) ABSTRACT

Computer system for calculating a pharmacokinetic behavior of a chemical substance in insects, comprising:
a physiologically based pharmacokinetic simulation model (102) of an insect for predicting concentration/time profiles of the chemical substance in compartments of the insect, the simulation model having at least one parameter which is dependent on the substance, and
a prediction module (110) for predicting the at least one parameter on the basis of a physicochemical property of the substance.

5 Claims, 4 Drawing Sheets

COMPUTER SYSTEM AND METHOD OF CALCULATING A PHARMACOKINETIC BEHAVIOR OF A CHEMICAL SUBSTANCE IN INSECTS

The invention relates to a computer system for calculating a pharmacokinetic behavior of a chemical substance in insects on the basis of a physiological model, as well as to a corresponding method and computer program product.

BACKGROUND OF THE INVENTION

Many physiologically based models for mammals are known from the prior art (for example, Charnick et al., J. Pharmacokin Biopharm. 23, 217 (1995)). A physiologically based model for caterpillars is furthermore known from the prior art (Greenwood et al., Pestic. Sci. 30, 97 (1990)). The insect is in this case described by compartments, which each represent an individual organ of the insect. The "interconnection" of the individual compartments is obtained from the known physiology of caterpillars. The essential parameters of this model are the rate coefficients for inter-compartmental mass transport, which determine the speed of the distribution, and the organ distribution coefficients, which give the concentration ratio in thermodynamic equilibrium between the respective organ and the haemolymph, which corresponds to the blood fluid in mammals.

It is known from the prior art to use such compartmental models in order to describe an experimentally determined pharmacokinetic profile of a substance retrospectively, by matching the rate coefficients and the distribution coefficients (for example, Lagadic et al., Pestic. Biochem. Physiol. 45, 105 (1993).& Pestic. Biochem. Physiol. 48, 173 (1994)).

It is therefore an object of the invention to provide a computer system for predicting the pharmacokinetic behavior of a chemical substance in an insect, as well as a corresponding method and computer program product.

The invention makes it possible, in a particularly efficient way, to calculate a prediction of the pharmacokinetic behavior of a chemical substance in an insect. In particular, the invention makes it possible to estimate the absorption, distribution and the excretion of chemical substances in insects on the basis of physicochemical parameters.

SUMMARY OF THE INVENTION

To this end, a physiologically based pharmacokinetic simulation model of an insect is used to predict concentration/time profiles of a chemical substance in the compartments of the insect. The simulation model contains at least one parameter which is dependent on the substance to be studied. The parameter or parameters of the simulation model are, for a particular substance, predicted on the basis of one or more of the physicochemical properties of the substance.

These physicochemical parameters are, for example, the lipophilicity of the substance, described by the distribution coefficient between water and phospholipid membranes or the octanol/water distribution coefficient, the molecular weight or the solubility. The relevant physicochemical parameters of the substance may either be determined by straightforward experiments or determined directly from the descriptor of the chemical structure of the substance by means of methods which are known per se, such as QSAR=Quantitative Structure Activity Relations, or neural networks.

In the latter case, it is even possible to evaluate virtual substances by the method according to the invention, that is to say substances which have not yet been synthesized, with respect to their absorption properties and distribution properties in insects. Owing to the established relationship between physicochemical properties and pharmacokinetic properties, it is furthermore possible to derive general criteria for the optimization of insecticidal agents.

According to a preferred embodiment of the invention the rate coefficient of the inter-compartmental mass transport, which is proportional to the product of the permeability for the substance and the effective surface area of the compartments, is used as a substance-dependent parameter of the simulation model. For each compartment of the simulation model, there is hence preferably a substance-dependent parameter which contains the permeability of the relevant compartment for the substance and the effective surface area of the relevant compartment. The permeability coefficient is a measure for the describing substance flux across the cellular membrane.

It is particularly advantageous that no further experimental studies are needed to determine the parameters for the simulation model based on a physicochemical property of the substance, but rather that the parameter or parameters can be determined on the basis of the physicochemical property of the substance. This determination is carried out on the basis of a database, which has been previously determined experimentally for various test substances. The database contains the substance-dependent parameters of the simulation model which have been experimentally determined for the test substances, as well as the physicochemical properties of the test substances. This database is used to predict the substance-dependent parameter or parameters for a substance to be studied.

According to a preferred embodiment of the invention, a calculation function is obtained from the database by a linear regression. For example, the calculation function is a function of the lipophilicity and the molecular weight. To predict a parameter for the simulation model for a substance to be studied, it is hence merely necessary for the lipophilicity and the molecular weight of the substance to be studied to be evaluated with the calculation function, in order to obtain the parameter. With the predicted parameter, it is then possible to carry out a concrete simulation of concentration/time profiles during absorption and excretion of the substance in the insect.

Alternatively, other prediction methods which are known per se may also be used instead of the calculation function obtained by linear regression.

It is particularly advantageous that, after a database has been determined once for a particular number of test substances, no additional experiments are then needed for simulation of the pharmacokinetic behavior of further substances. This makes it possible to assess "candidates" for potential insecticides in respect of their pharmacokinetic behavior with a high throughput. Significant acceleration for research, development and optimization of new insecticides is therefore possible.

BRIEF DESCRIPTION OF THE DRAWINGS

Preferred embodiments of the invention will be explained in more detail below with reference to the drawings, in which:

FIG. 1 shows a computer system 100. It may be a conventional personal computer (PC), a workstation or a client/server system.

Figure 1:
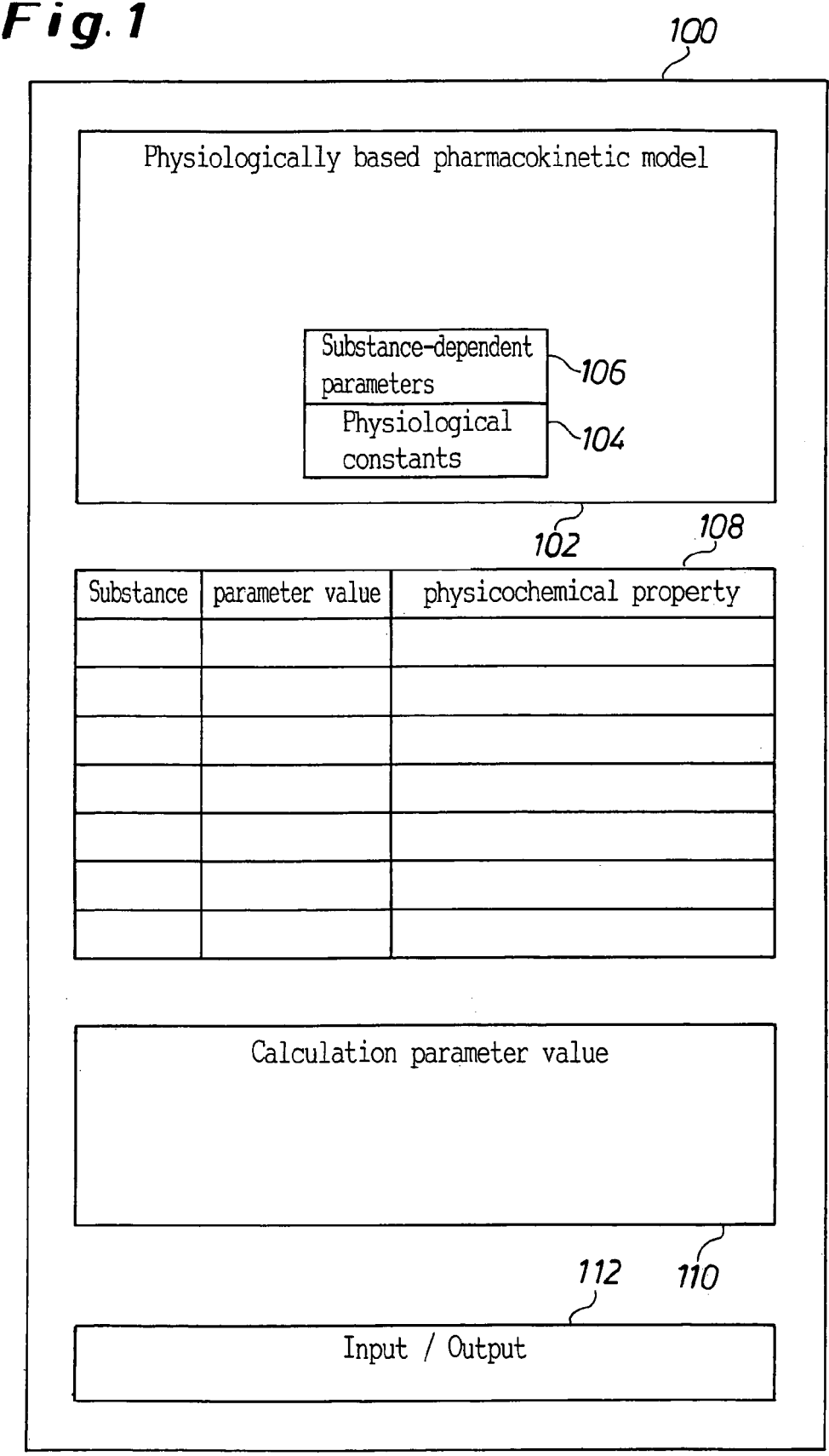
FIG. 1 shows a block diagram of an embodiment of a computer system according to the invention.

The computer system 100 has a simulation model 102. This is a physiologically based pharmacokinetic model of an insect. To this end, the simulation model 102 represents the compartments of the insect, and hence makes it possible to predict concentration/time profiles of a substance in the compartments of the insect.

The simulation model 102 involves physiological parameters, 104 which depend only on the type of insect to be described, as well as one or more substance-dependent parameters 106. To carry out a simulation calculation of concentration/time profiles, it is hence necessary to input the parameter value of the substance-dependent parameter 106 for the substance to be evaluated. A concrete example of an embodiment of the simulation model 102 will be explained in more detail below with reference to FIGS. 3 and 4.

The computer system 100 furthermore has a databank 108. The databank 108 is used for storing a database, which have been obtained on the basis of experimental studies of the pharmacokinetic behavior of test substances in the insect. For each of the test substances previously studied experimentally, the databank 108 contains the parameter value or values which have been experimentally determined for the relevant test substance, as well as at least one physicochemical property of the relevant test substance.

This database stored in the databank 108 forms the basis of the prediction of the parameter value for a new substance to be studied in the prediction module 110. A calculation rule, which makes it possible to obtain the substance-dependent parameter value needed for carrying out the simulation with the simulation model 102 from a physicochemical property of a substance to be studied, for example its lipophilicity or its molecular weight, is for example obtained by a linear regression method from the database stored in the databank 108.

The computer system 100 furthermore has an input/output module 112 for input of the physicochemical property of a substance to be studied. The simulated concentration/time profiles are furthermore output via the input/output module 112.

The input/output module 112 may be coupled to a databank which contains descriptors of substances which actually exist or virtual substances, for example potential insecticides, and their physicochemical properties. In the case of virtual substances which have not yet been synthesized, the physicochemical property required for input into the computer system 100 may be determined directly from the descriptor of the chemical structure of the test substance by means of methods which are known per se, such as QSAR, or neural networks. In the case of virtual substances, the descriptor instead of the physicochemical property may also be input via the input/output module 112. On the basis of the descriptor, the physicochemical property is then determined as an input quantity of the prediction module 110 in the computer system 100 itself.

The simulation results are, for example, input into the database via the input/output module 112 so that evaluation of the simulation results can be carried out at a later time.

Figure 2:
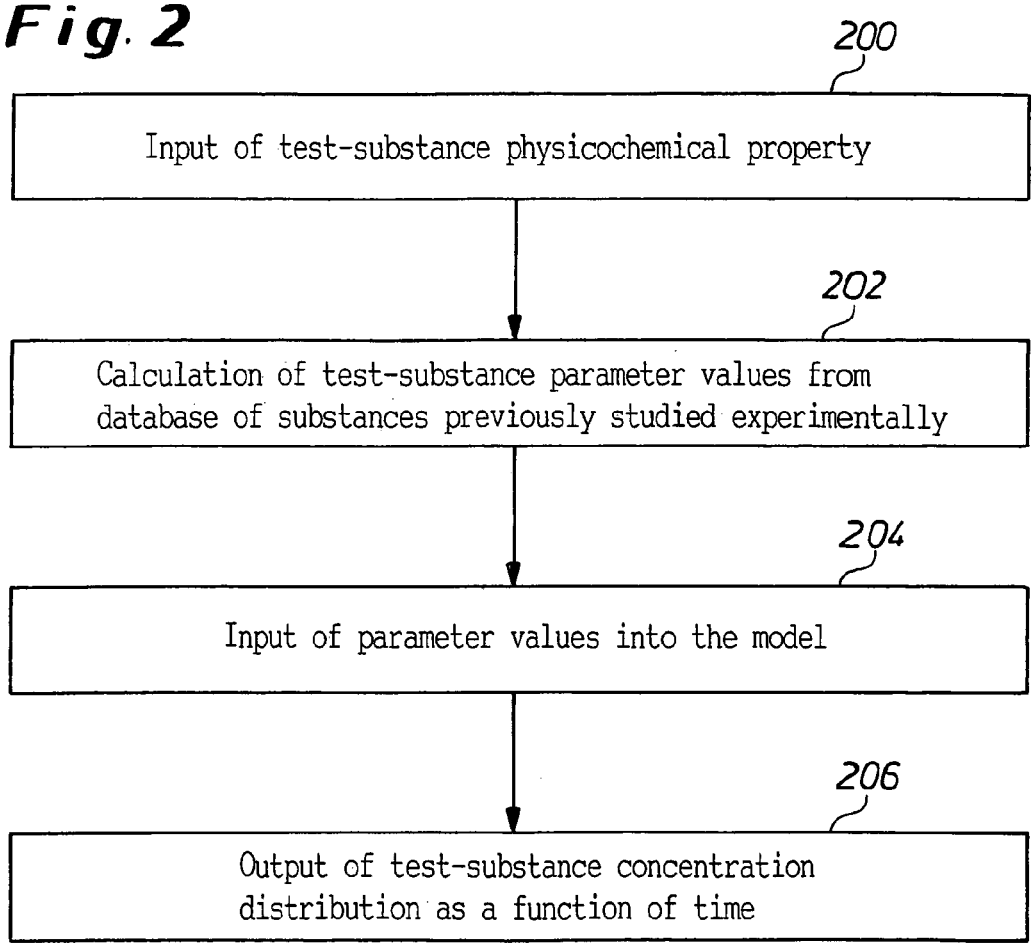
FIG. 2 shows a flow chart of an embodiment of the method according to the invention.

FIG. 2 shows a corresponding flow chart. In step 200, a physicochemical property of a substance to be studied is input. The physicochemical property is, for example, the lipophilicity or the molecular weight of the substance.

In step 202, the parameter values of the substance-dependent parameters of the simulation model for the substance are calculated on the basis of a database based on the physicochemical property of the substance to be assessed. This database contains parameter values previously determined experimentally for various test substances. This calculation is carried out in step 202.

In step 204, the parameters calculated in step 202 are input into the simulation model. The calculation of concentration/time profiles of the substance to be studied in the compartments of the insect is then carried out there. In step 206, these concentration/time profiles are output and can then be evaluated.

In order to determine a database which is as meaningful as possible for prediction of the parameter values, it is advantageous if the test substances used to experimentally determine the database are as chemically diverse as possible. A new substance to be studied, for which the parameter values are to be predicted, should preferably lie within the test space represented by the test substances.

Figure 3:
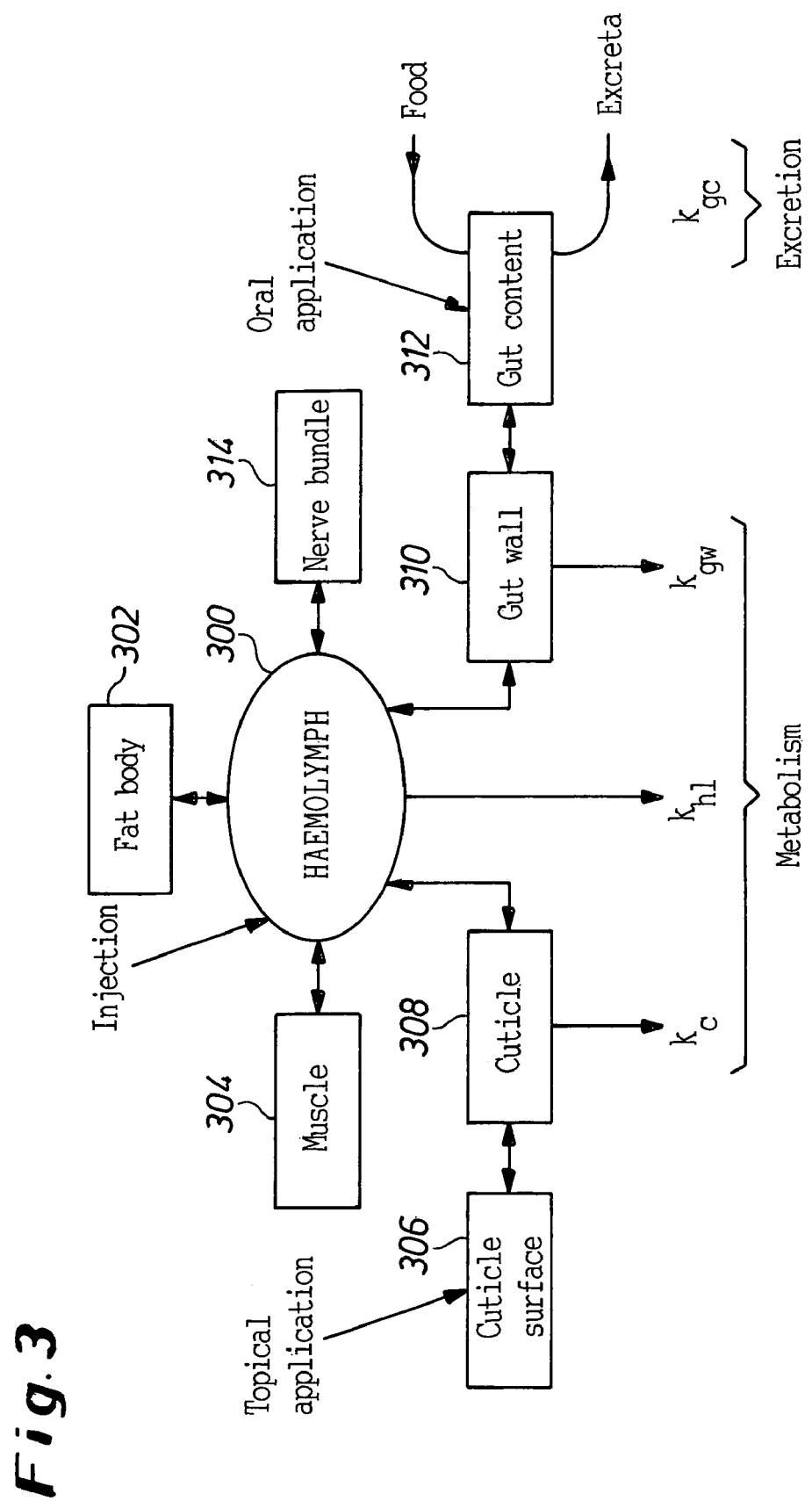
FIG. 3 shows a physiologically based model of a caterpillar as a basis for a simulation model according to the invention with a substance-dependent parameter.

FIG. 3 shows, by way of example, a physiological model for a caterpillar. This physiological module is based on the model given by Greenwood et al. (see above).

The model involves the following eight compartments of the caterpillar: haemolymph (hl) 300, fat body (fb) 302, muscle (ms) 304, surface of the cuticle (cs) 306, cuticle (c) 308, gut wall (gw) 310, gut content (gc) 312 and nerve bundle (nc). A substance to be studied is applied either topically via the cuticle 308, orally via the gut or by direct injection into the haemolymph 300.

Like the blood in mammals, the haemolymph 300 is used as the main transport phase between the various organs.

Metabolism takes pace at the rate kc in the cuticle 308, at the rate khl in the haemolymph 300 and at the rate kgw in the gut wall 310. The excretion takes place at the rate $k_{gc}$.

The haemolymph 300 is modeled as a freely circulating liquid, which is in contact with the caterpillar organs described by the compartments. Transport processes between the compartments take place by passive diffusion, with permeation through the membranes as the rate-limiting step. The rate coefficients $\lambda_x$ of the mass transport between the compartments are determined by the permeability-surface area product $P_x A_x$ and the volume $V_x$ of the organs:

$$\lambda_x = \frac{P_x A_x}{V_x} \qquad (x \in \{c, mu, fb, nc, gw\}) \qquad (1)$$

where $P_x$=Permeability of the membrane (walls) of organ X for the substance, and $A_x$=surface area of the membrane (walls) of organ X.

c=cuticle, mu=muscle, fb=fat body, nc=nerve bundle gw=gut wall

The equilibrium state is in this case reached after a time $t_x \gg V_x/(P_x A_x)$. The ratio of the concentrations in the peripheral compartments in the equilibrium state is in this case determined by the distribution coefficients related to the haemolymph $K_x$ is defined as $K_{x/hl}$:

$$K_x = \frac{C_x}{C_{hl}} \qquad (x \in \{c, mu, fb, nc, gw\}) \qquad (2)$$

$K_x$ is hence the distribution coefficient of a substance between the haemolymph and the organ x in the equilibrium state.

In addition, the distribution coefficients between the surface of the cuticle 306 and the cuticle ($K_{c/cs}$) as well as the distribution coefficient between the gut wall 310 and the gut content ($K_{gc/gw}$) must be known.

The model with eight compartments which is known from Greenwood et al. has been modified in order to take account of

- different types of application (oral, topical or by injection into the haemolymph),
- an "open-loop" mass transport of food through the alimentary canal and
- the time dependency of the organ volumes due to the larval growth.

On the basis of this biophysical model of FIG. 3, it is possible to describe a mass equilibrium relation for each organ x of the caterpillar by a differential equation. Such mass equilibrium relations are given for the organs of the caterpillar in the appendix (Formulae A1 to A8).

In order to calculate a pharmacokinetic profile by means of the mass equilibrium relations of the organs of the caterpillar, a total of 23 parameter values must be known. They are

- the organ volumes $V_x$ (eight parameter values as well as additional parameter values for describing their time variations due to the larval growth),
- the distribution coefficients $K_x$ of the substance between the haemolymph 300 and the peripheral compartments (c, mu, fb, nc and gw),
- the distribution coefficients between the surface of the cuticle and the cuticle, as well as between the gut wall and the gut content,
- the metabolic rate constants in the cuticle, the haemolymph and the gut wall, in the event that the substance to be studied is metabolized, and
- rate coefficients $\lambda_x = [P_x A_x]/V_x$ for the mass transport between the compartments (c, mu, fb, nc and gw).

The distribution coefficients as well as the permeability-surface area products, and therefore the rate coefficients, depend on physiological parameters of the insect, as well as on the physicochemical properties of the substance to be studied. The metabolic rate constants are furthermore substance-specific.

The organ volumes can be experimentally determined by methods which are known per se. We can calculate the distribution coefficients $K_x$ of the substance between the haemolymph and each organ x as follows:

$$K_x = \frac{K_{x/H_2O}}{K_{hl/H_2O}} \text{ with } K_{x/H_2O} = f_{water,x} + K_{fat}f_{fat,x} + K_{protein}f_{protein,x} \qquad (3)$$

in which $K_{fat}$=distribution coefficient of the substance in equilibrium between water and fat (lipophilicity)

$K_{protein}$=distribution coefficient of the substance in equilibrium between water and protein $f_{water,x}$=volume fraction of water in compartment x,
$f_{fat,x}$=volume fraction of fat in compartment x,
$f_{protein,x}$=volume fraction of protein in compartment x.

The membrane affinity (MA) or, alternatively, the octanol/water distribution coefficient ($K_{o/w}$) of the substance can be used as an estimate of the distribution coefficients $K_{fat}$. The distribution coefficient $K_{protein}$ may, for example, be determined from the binding constants of human serum albumin ($K_d^{HSA}$ in [mmol]) and the molecular weight of the protein (65 kDa):

$$HSA = \frac{1}{K_d^{HSA}} \bigg/ 65 \qquad (4)$$

Formula 3 can be simplified by combining the fat and protein fractions in a single organic fraction:

$$K_x = \frac{K_{x/H_2O}}{K_{hl/H_2O}} \text{ with } K_{x/H_2O} = f_{water,x} + (1 - f_{water,x})K_{fat} \qquad (5)$$

The rate constants of the mass transport between the compartments are experimentally determined for the test substances by matching them to experimental pharmacokinetic data and correlating them with the physicochemical properties of the test substances.

As an approximation, it may be assumed that the permeability coefficient P for the substance is identical for all the organs x, in that is to say Px=P for all the organs x, with the exception of the cuticle. Furthermore, P is proportional to the lipophilicity ($K_{fat}$=MA or $K_{fat}=K_{o/w}$, that is to say the octanol/water distribution coefficient) and the membrane diffusion coefficient $D_{mem}$ of the substance:

$$P \propto K_{fat} D_{mem} \qquad (6)$$

The dependency of the membrane diffusion coefficient on the molecular weight (MW) of the substance is described by means of an exponential relation:

$$D_{mem} \propto MW^{-s_{mem}} \qquad (7)$$

Formulae 6 and 7 can be combined with one another, so that $$P = \alpha K_{fat} MW^{-s_{mem}} \qquad (8)$$

results, in which α is a constant. By means of Equation 1 the rate constants of the mass transport between the compartments can be expressed as follows:

$$\lambda_x = \alpha \frac{A_x}{V_x} K_{fat} MW^{-s_{mem}} \qquad (9)$$

the following is obtained from this by taking a logarithms $$\text{Log}\left(\frac{\lambda_x}{K_{fat}}\right) = \text{Log}\left(\alpha \frac{A_x}{V_x}\right) - s_{mem}\text{Log}(MW) \qquad (10)$$

Figure 4:
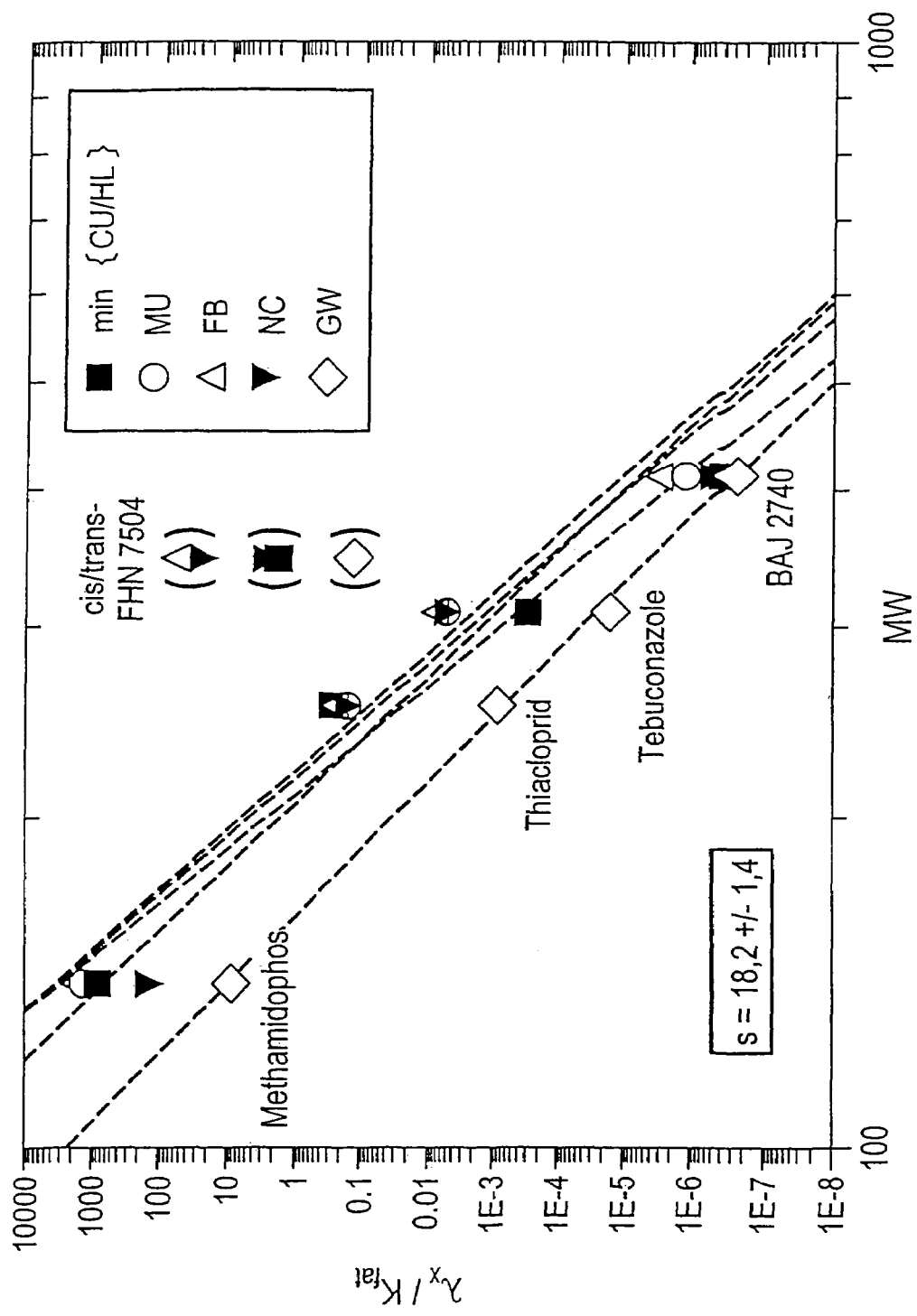
FIG. 4 shows a diagram representing the database obtained for the simulation model of FIG. 3 for carrying out a linear regression, in order to determine a calculation function.

FIG. 4 shows a corresponding logarithm/logarithm representation of $\lambda_x/K_{fat}$ against the molecular weight MW of a plurality of test substances for various compartments. FIG. 4 likewise shows the best-fit lines obtained by linear regressions through the measurement points.

By means of linear regression, it is hence possible to determine the slope $S_{mem}$ as well as the intercept $\alpha A_x/V_x$ from the experimentally determined database. A calculation rule has therefore be obtained which makes it possible to calculate the quantity $\lambda_x$ of a new substance, even a virtual one, merely on the basis of the lipophilicity ($K_{fat}$) and molecular weight MW. $P \cdot A_x$ is hence obtained on the basis of Formulae 8 and 9. On the basis of this substance-dependent parameter, as well as the equilibrium distribution coefficients $K_x$ or $K_{c/cs}$ and $K_{gc/gw}$ from Eqs (3) and (5) respectively, it is hence possible to solve the system of equations in the appendix, for example numerically, and the time/concentration profiles of the substance to be studied in the individual compartments are obtained.

Appendix

System of equations of the pharmacokinetic simulation model for the caterpillar $$(cs)\quad V_{cs}\frac{dC_{cs}}{dt} = -[PA]_c\left(C_{cs} - \frac{C_c}{K_{c/cs}}\right) \tag{A1}$$

$$(c)\quad V_c\frac{dC_c}{dt} = [PA]_c\left(C_{cs} - \frac{C_c}{K_{c/cs}}\right) + \tag{A2}$$
$$[PA]_c\left(C_{hl} - \frac{C_c}{K_c}\right) - k_c C_c$$

$$(hl)\quad V_{hl}\frac{dC_{hl}}{dt} = -\sum_x [PA]_x\left(C_{hl} - \frac{C_x}{K_x}\right) - k_{hl} C_{hl} \tag{A3}$$
$$(x \in \{c, mu, fb, nc, gw\})$$

$$(mu)\quad V_{mu}\frac{dC_{mu}}{dt} = [PA]_{mu}\left(C_{hl} - \frac{C_{mu}}{K_{mu}}\right) \tag{A4}$$

$$(fb)\quad V_{fb}\frac{dC_{fb}}{dt} = [PA]_{fb}\left(C_{hl} - \frac{C_{fb}}{K_{fb}}\right) \tag{A5}$$

$$(nc)\quad V_{nc}\frac{dC_{nc}}{dt} = [PA]_{nc}\left(C_{hl} - \frac{C_{nc}}{K_{nc}}\right) \tag{A6}$$

$$(gw)\quad V_{gw}\frac{dC_{gw}}{dt} = [PA]_{gw}\left(C_{hl} - \frac{C_{gw}}{K_{gw}}\right) - \tag{A7}$$
$$[PA]_{gw}\left(C_{gw} - \frac{C_{gc}}{K_{gc/gw}}\right) - k_{gw} C_{gw}$$

$$(gc)\quad V_{gc}\frac{dC_{gc}}{dt} = [PA]_{gw}\left(C_{gw} - \frac{C_{gc}}{K_{gc/gw}}\right) \tag{A8}$$

$C_x$: concentration of the substance in compartment x, $V_x$: volume of compartment x; the volume may be time-variant according to an experimentally determined function ($V_x(t)$), $[PA]_x$: permeability-surface area product of compartment x, $K_{x/y}$: distribution coefficient between compartments x and y, $K_x \equiv K_{x/hl}$: distribution coefficient between organ x and haemolymph, $K_x$: rate constants for the metabolism (x=c, hl, gw)

List of References

Computer system 100
simulation model 102
Physiological constants 104
Substance-dependent parameter 106
Database 108
Prediction module 110
Input/output module 112
Haemolymph (hl) 300
Fat body (fb) 302
Muscle (mu) 304
Surface of the cuticle (cs) 306
Cuticle (c) 308
Gut wall (gw) 310
Gut content (gc) 312
Nerve bundle (nc) 314

We claim:

1. A computer system for calculating a pharmacokinetic behavior of a chemical substance in an insect based on at least one physicochemical property of said chemical substance, the computer system comprising:
    a physiologically based pharmacokinetic simulation model of said insect for predicting pharmacokinetic behaviors, comprising predicting concentration/time profiles of the chemical substance, the physiological based pharmacokinetic simulation model being represented by a system of coupled differential equations, the differential equations describing the mass transport, the distribution, the metabolism and the excretion of chemical substances in said insect on the basis of the following substance-dependent parameters:
    rate coefficients for mass transport between the organs of said insect, organ/haemolymph distribution coefficients, metabolism rate coefficients, and excretion rate coefficients;
    a database containing physicochemical properties and experimentally determined substance-dependent parameters of chemical substances and further containing relationships, concentration/time profiles and coefficients required for the pharmacokinetic simulation model;
    a prediction module for calculating the substance-dependent parameters of the chemical substance to be studied, which are required by the physiological based pharmacokinetic simulation model, from at least one physicochemical property of the substance by means of the relationships stored in said database;
    an input/output module for the input of at least one physicochemical property of a chemical substance to be studied;
    and for the output of a calculated pharmacokinetic behavior of a chemical substance in an insect, comprising a simulated concentration/time profile of the chemical substance to a user of said computer system.

2. Computer system according to claim 1, wherein said physicochemical property is the distribution coefficient between water and phospholipid membranes, the octanol/water distribution coefficient, the molecular weight, the solubility, and/or a combination of these parameters of the substance.

3. Computer system according to claim 1, wherein the physicochemical properties of chemical substances and corresponding substance-dependent parameters are stored in the database and are used to obtain a calculation function for prediction of substance-dependent parameters for a new substance to be studied.

4. Computer system according to claim 1, wherein the prediction module includes a calculation function for calculating the substance-dependent parameters required by the physiological based pharmacokinetic simulation model from the lipophilicity and/or the molecular weight of the substance.

5. Computer system according to claim 4, wherein the calculation function is based on a linear regression of experimentally determined parameter values.

* * * * *